(12) United States Patent
Muto (10) Patent No.: US 9,538,916 B2
(45) Date of Patent: Jan. 10, 2017

(54) FUNDUS INSPECTION APPARATUS (75) Inventor: Kenji Muto, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 534 days.

(21) Appl. No.: 13/413,927

(22) Filed: Mar. 7, 2012

(65) Prior Publication Data

US 2012/0249961 A1    Oct. 4, 2012

(30) Foreign Application Priority Data

Mar. 31, 2011    (JP) .................................. 2011-077097

(51) Int. Cl.
*A61B 3/15*    (2006.01)
*A61B 3/10*    (2006.01)

(52) U.S. Cl.
CPC ............... *A61B 3/152* (2013.01); *A61B 3/102* (2013.01)

(58) Field of Classification Search
CPC ........ A61B 3/0075; A61B 3/152; A61B 3/102
USPC ......................................................... 351/208
See application file for complete search history.

(56) References Cited

U.S. PATENT DOCUMENTS

| | | | |
|---|---|---|---|
| 5,526,072 A | 6/1996 | El Hage | |
| 6,206,523 B1 | 3/2001 | Hino | |
| 6,337,920 B1 | 1/2002 | Mühlhoff | |
| 7,784,942 B2 * | 8/2010 | Maeda et al. | 351/206 |
| 7,794,083 B2 | 9/2010 | Tsukada et al. | |
| 8,398,236 B2 * | 3/2013 | Juhasz et al. | 351/206 |
| 2005/0246642 A1 * | 11/2005 | Valderas | G06F 3/0481 715/730 |
| 2008/0151187 A1 | 6/2008 | Tsukada et al. | |
| 2010/0103374 A1 | 4/2010 | Hirose et al. | |
| 2010/0110172 A1 | 5/2010 | Satake | |
| 2010/0321700 A1 | 12/2010 | Hirose et al. | |

(Continued)

FOREIGN PATENT DOCUMENTS

CN    101204318 A    6/2008
EP    2 184 006 A1    5/2010

(Continued)

OTHER PUBLICATIONS

Carl Zeiss Meditec. Cirrus HD-OCT User Manual. Dublin, CA: Carl Zeiss Meditec, 2009. Print.*

(Continued)

*Primary Examiner* — Zachary Wilkes
(74) *Attorney, Agent, or Firm* — Fitzpatrick, Cella, Harper & Scinto (57) ABSTRACT

In an OCT device, even if an alignment according to a pupil center and a position where a tomographic image can be photographed at a good position may be different according to a subject, automatic alignment is continued at a position where an image quality is good. In a fundus inspection apparatus, an initial adjustment target position on an obtained anterior ocular segment image and an optical axis of a measurement optical system are coincided with each other, and then initial position adjustment is performed. When an instruction for moving an initial adjustment target position is issued, the measurement optical system is moved by a moving amount corresponding to the instruction. At the same time, the initial adjustment target position on the anterior ocular segment image is changed to a position after the movement of the measurement optical system, and positional adjustment is performed again.

11 Claims, 7 Drawing Sheets

(56) References Cited

U.S. PATENT DOCUMENTS

| | | | |
|---|---|---|---|
| 2011/0199579 A1 | 8/2011 | Muto | |
| 2011/0205490 A1 | 8/2011 | Murata et al. | |
| 2011/0286003 A1 | 11/2011 | Ono | |
| 2012/0092617 A1* | 4/2012 | Muto | A61B 3/102 351/206 |
| 2012/0121158 A1 | 5/2012 | Sekine et al. | |

FOREIGN PATENT DOCUMENTS

| | | |
|---|---|---|
| JP | 2000-245698 A | 9/2000 |
| JP | 2010-181172 A | 8/2010 |
| JP | 2010-220772 A | 10/2010 |
| JP | 2010-233998 A | 10/2010 |
| WO | 2010/089833 A1 | 8/2010 |
| WO | 2010/150496 A1 | 12/2010 |
| WO | 2011/013314 A1 | 2/2011 |

OTHER PUBLICATIONS

Apr. 1, 2014 Chinese Official Action in Chinese Patent Appln. No. 201210096410.1.

European Search Report dated Jul. 16, 2012, in European Patent Application No. 12162334.2.

D.M. Stein, et al., "A new quality assessment parameter for optical coherence tomography", British Journal of Ophthalmology, 2006, vol. 90, pp. 186-190.

Feb. 2, 2015 Chinese Official Action in Chinese Patent Appln. No. 201210096410.1.

* cited by examiner

FUNDUS INSPECTION APPARATUS

BACKGROUND OF THE INVENTION

Field of the Invention

The present invention relates to a fundus inspection apparatus used for photographing a surface image and a tomographic image of a fundus of an eye to be inspected.

Description of the Related Art

Recently, there has been put to practical use a device (hereinafter also referred to as an OCT device) using an optical coherence tomography (OCT) in which a tomographic image is photographed by utilizing interference due to low coherence light. In this device, since the tomographic image can be photographed with about the same resolution as the wavelength of light entering an object to be inspected, the tomographic image of the object to be inspected can be obtained with a high resolution. The OCT device is particularly useful as an ophthalmic device for obtaining a tomographic image of a retina in a fundus.

Meanwhile, in an ophthalmic device at large, regardless of inspection of a fundus, it is important to highly accurately align an inspection portion (mainly, measurement optical system) of the device with respect to an eye to be inspected for photographing.

Japanese Patent Application Laid-Open No. 2000-245698 discloses an eye refractive power measurement apparatus which, when the eye is opacified due to cataract, for example, drives a measurement portion with respect to the eye to be inspected to receive, at each measurement position, light returned from a fundus by a sensor, and, thus, to predict whether measurement can be performed well based on the amount of the received light, whereby the measurement is performed at a good position.

Japanese Patent Application Laid-Open No. 2010-181172 discloses an optical image measurement device which is an OCT device automatically photographing a tomographic image when alignment is in a good state.

When the device disclosed in the Japanese Patent Application Laid-Open No. 2000-245698 is applied to the OCT device, the inspection time is relatively long because of various scanning operations. Therefore, when involuntary eye movement continuously occurs, an optimum position is required to be automatically found at every involuntary eye movement, so that there is a problem that the alignment time is increased.

In the Japanese Patent Application Laid-Open No. 2010-181172, although an automatic alignment of the eye to be inspected is described, a specific configuration is not described.

Thus, in the OCT device in which the inspection time per subject is relatively long, continuous automatic alignment is desired.

In many cases, the alignment with respect to the eye to be inspected is performed, regardless of manually or automatically, by detecting a pupil center position of an anterior eye portion and aligning an optical axis of a measurement portion with respect to the pupil center position. However, in such case, a tomographic image of a fundus may be darkened according to the eye to be inspected. In such case, in a manual OCT device, it is necessary that an operator perform fine adjustment to improve the tomographic image of the fundus.

In this regard, there is no OCT device which continuously performs automatic alignment, nor is there OCT device in which good images are continuously obtained.

SUMMARY OF THE INVENTION

In view of the above problems, the present invention provides a fundus inspection apparatus which has a tomographic image acquisition unit which obtains a tomographic image of an eye to be inspected based on multiplexed light obtained by multiplexing return light from the eye to be inspected, irradiated with measurement light, and reference light corresponding to the measurement light, a relative position changing unit which changes a relative position between an optical axis of an optical system irradiating the eye to be inspected and a center position of an anterior ocular segment image of the eye to be inspected, a designating unit which designates a predetermined position of the anterior ocular segment image when the relative position is within a first predetermined range, and a control unit which controls the relative position changing unit so that the relative position between the optical system irradiating the eye to be inspected and the predetermined position is within a second predetermined range.

In the fundus inspection apparatus of the present invention, automatic alignment with respect to a position where a good tomographic image can be photographed can be performed continuously. From the standpoint of an operator, the operator can easily use the fundus inspection apparatus, and the inspection time is shortened to reduce the burden of a subject.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Example 1

A fundus inspection apparatus in this example is an OCT device having an automatic alignment function, automatically determines a position where a good tomographic image can be photographed, and can continuously perform automatic alignment at the position.

(Schematic Configuration of Device)

Figure 2A:
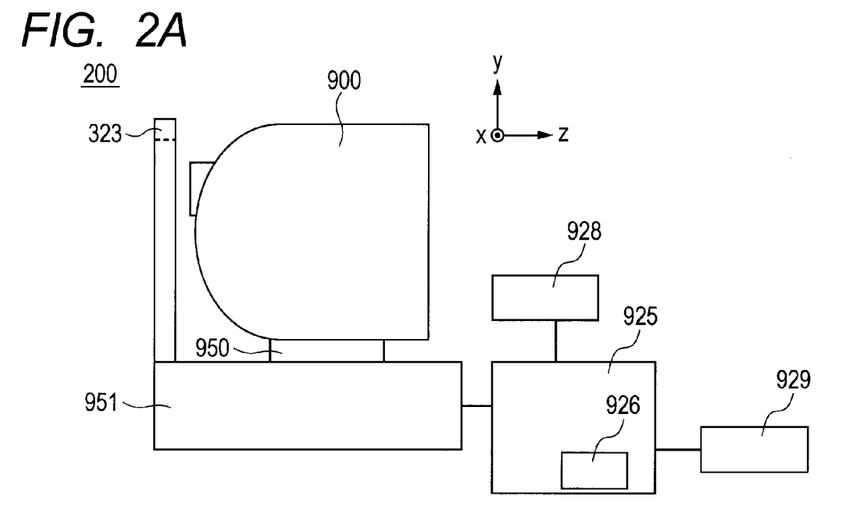
FIGS. 2A and 2B are views for explaining a fundus inspection apparatus in the examples 1 and 2.

A schematic configuration of the fundus inspection apparatus in this example will be described using FIG. 2A. FIG.

2A is a side view of an ophthalmic device. An ophthalmic device 200 which is a fundus inspection apparatus is provided with an optical head 900, a stage portion 950, and a base portion 951. The optical head 900 is a measurement optical system for photographing an anterior ocular segment image, a two-dimensional image of a fundus, and a tomographic image. The stage portion 950 is a moving portion which can be moved in x, y, and z directions in FIG. 2A by using a motor (not shown). The base portion 951 incorporates a spectroscope to be described later.

The ophthalmic device 200 is further provided with a personal computer 925 serving as a movement control portion which controls the movement of the stage portion and functioning as a device control portion which controls the stage portion and configures a tomographic image, for example. In the ophthalmic device 200, a hard disk 926 serves as a subject information storage portion and stores programs for tomographic photographing. A monitor 928 is a display portion, and an input portion 929 provides instructions to the personal computer and is, specifically, constituted of a keyboard and a mouse. A chin stage 323 fixes the chin and the forehead of a subject and thereby fixes of the eye of the subject (the eye to be inspected).

(Configuration of Measurement Optical System and Spectroscope)

Figure 2B:
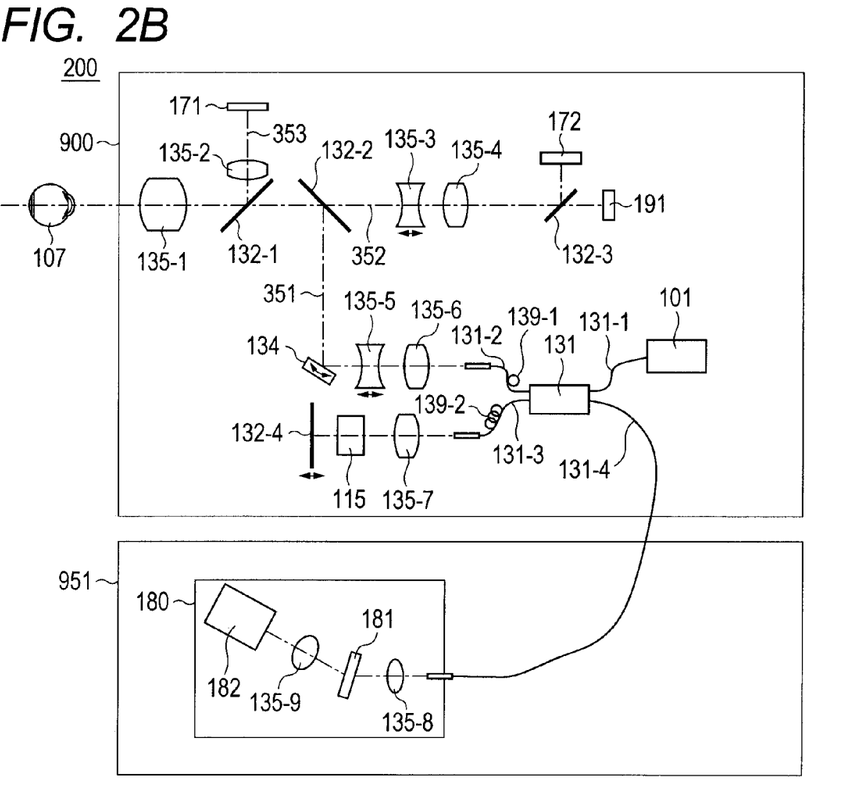

The configuration of the measurement optical system and the spectroscope in this example will be described using FIG. 2B. First, the inside of the optical head 900 will be described. An objective lens 135-1 is installed so as to face an eye to be inspected 107, and an optical path is branched on the optical axis, for each wavelength band, into an optical path 351 of an OCT optical system, an optical path 352 for fundus observation and a fixation lamp, and an optical path 353 for anterior eye observation by a first dichroic mirror 132-1 and a second dichroic mirror 132-2.

Similarly to above, the optical path 352 is branched, for each wavelength band, into an optical path to a CCD 172 for fundus observation and an optical path to a fixation lamp 191 by a third dichroic mirror 132-3. The ophthalmic device 200 includes lenses 135-3 and 135-4, and the lens 135-3 is driven by a motor (not shown) for the purpose of focusing for the fixation lamp and fundus observation. The CCD 172 has a sensitivity near the wavelength of illumination light for fundus observation (not shown), specifically near 780 nm. Meanwhile, the fixation lamp 191 generates visible light to prompt fixation of the subject.

In the optical path 353, a lens 135-2 and an infrared CCD 171 for anterior eye observation are provided. The CCD 171 has a sensitivity near the wavelength of illumination light for anterior eye observation (not shown), specifically near 970 nm.

As described above, the optical path 351 constitutes the OCT optical system and is used for photographing the tomographic image of the fundus of the eye to be inspected 107. More specifically, the optical path 351 is used for obtaining an interference signal for the formation of the tomographic image. An XY scanner 134 scans light on the fundus. Although the XY scanner 134 is illustrated as a single mirror, it performs scanning in the XY biaxial directions. Among lenses 135-5 and 135-6, the lens 135-5 is driven by a motor (not shown) to focus light from a light source 101, emitted from a fiber 131-2 connected to an optical coupler 131, onto the fundus 107. By virtue of the focusing, the light beams from the fundus 107 are simultaneously converted into a spot-like image at an end of the fiber 131-2 and then entered.

Next, the configurations of an optical path from the light source 101, a reference optical system, and a spectroscope will be described.

There are provided a light source 101, a mirror 132-4, a glass for dispersion compensation 115, the optical coupler 131, single-mode optical fibers 131-1 to 131-4 unified by being connected to the optical coupler, a lens 135-7, and a spectroscope 180.

A Michelson interferometer is constituted by the above configurations. The light emitted from the light source 101 passes through the optical fiber 131-1 and is branched through the optical coupler 131 into measurement light passing through the optical fiber 131-2 and reference light passing through the optical fiber 131-3. The measurement light is applied to the fundus of the eye to be inspected 107 as an observation object through the OCT optical system optical path and reaches the optical coupler 131 through the same optical path by being reflected and scattered by a retina.

Meanwhile, the reference light reaches the mirror 132-4 through the optical fiber 131-3, the lens 135-7, and a dispersion compensation glass 115, inserted for matching the dispersions of the measurement light and the reference light, to be reflected by the mirror 132-4, and, thus, to return to the optical coupler 131 through the same optical path.

By virtue of the optical coupler 131, the measurement light and the reference light are combined to become combined light (interference light). When the optical path length of the measurement light and the optical path length of the reference light are substantially the same, interference occurs. The mirror 114 is held so as to be adjustable in the optical axis direction by a motor and a drive mechanism (not shown) and can adjust the optical path length of the reference light to the optical path length of the measurement light changed according to the eye to be inspected 107. The interference light is led to the spectroscope 180 through the optical fiber 131-4. A polarization adjustment portion 139-1 on the measurement light side is provided in the optical fiber 131-2. A polarization adjustment portion 139-2 on the reference light side is provided in the optical fiber 131-3. Those polarization adjustment portions have some portions where the optical fiber is routed into a loop, and the looped portions are rotated around the longitudinal direction of the fiber to twist the fiber, whereby the respective polarization states of the measurement light and the reference light are adjusted and can be matched each other. In this device, the polarization states of the measurement light and the reference light are previously adjusted and fixed.

The spectroscope 180 is constituted of lenses 135-8 and 135-9, a diffraction grating 181, and a line sensor 182.

The interference light emitted from the optical fiber 131-4 becomes parallel light through the lens 135-8 to be then branched by the diffraction grating 181, and, thus, to be focused on the line sensor 182 by the lens 135-9.

Next, the periphery of the light source 101 will be described. The light source 101 is an SLD (Super Luminescent Diode) which is a typical low coherent light source. The center wavelength is 855 nm, and the wavelength band width is about 100 nm. The band width affects the resolution in the optical axis direction of the resulting tomographic image and hence is an important parameter. Although the SLD is selected as a type of the light source in this example, ASE (Amplified Spontaneous Emission), etc. may also be used so far as it can emit low coherent light. In view of the measurement for the eyes, near infrared rays are suitable as the center wavelength. The center wavelength affects the resolution in a transverse direction of the resulting tomographic image and hence is desirably as short wavelength as possible. For the two reasons, the center wavelength in this example is 855 nm.

In this example, although the Michelson interferometer is used as an interferometer, a Mach-Zehnder interferometer may be used. When a light quantity difference is large corresponding to the light quantity difference between the measurement light and the reference light, the Mach-Zehnder interferometer is preferably used. When the light quantity difference is small, the Michelson interferometer is preferably used.

(Method of Photographing Tomographic Image)

A method of photographing a tomographic image with the use of a fundus inspection apparatus 200 will be described. The fundus inspection apparatus 200 controls the XY scanner 134 and thereby can photograph the tomographic image of a desired portion of the fundus of the eye to be inspected 107.

First, the measurement light is scanned in the X direction in the drawings, and information of a predetermined number of times of photographing is photographed by the line sensor 182 from a photographing range in the X direction in the fundus. The brightness distribution on the line sensor 182 obtained at a certain position in the X direction undergoes FFT, and an image converted into concentration or color information for displaying the linear brightness distribution, obtained by FFT, on a monitor 928 is referred to as an A-scan image. A two-dimensional image in which a plurality of the A-scan images are arranged is referred to as a B-scan image. After photographing of the plurality of A-scan images for building the single B-scan image, the scan position in the Y direction is moved, and the scanning in the X direction is performed again, whereby a plurality of the B-scan images are obtained. The plurality of B-scan images or a three-dimensional tomographic image built from the B-scan images is displayed on the monitor 928, whereby an operator can use the image for diagnosis of the eye to be inspected.

(Flow of Photographing Tomographic Image)

Figure 1A:
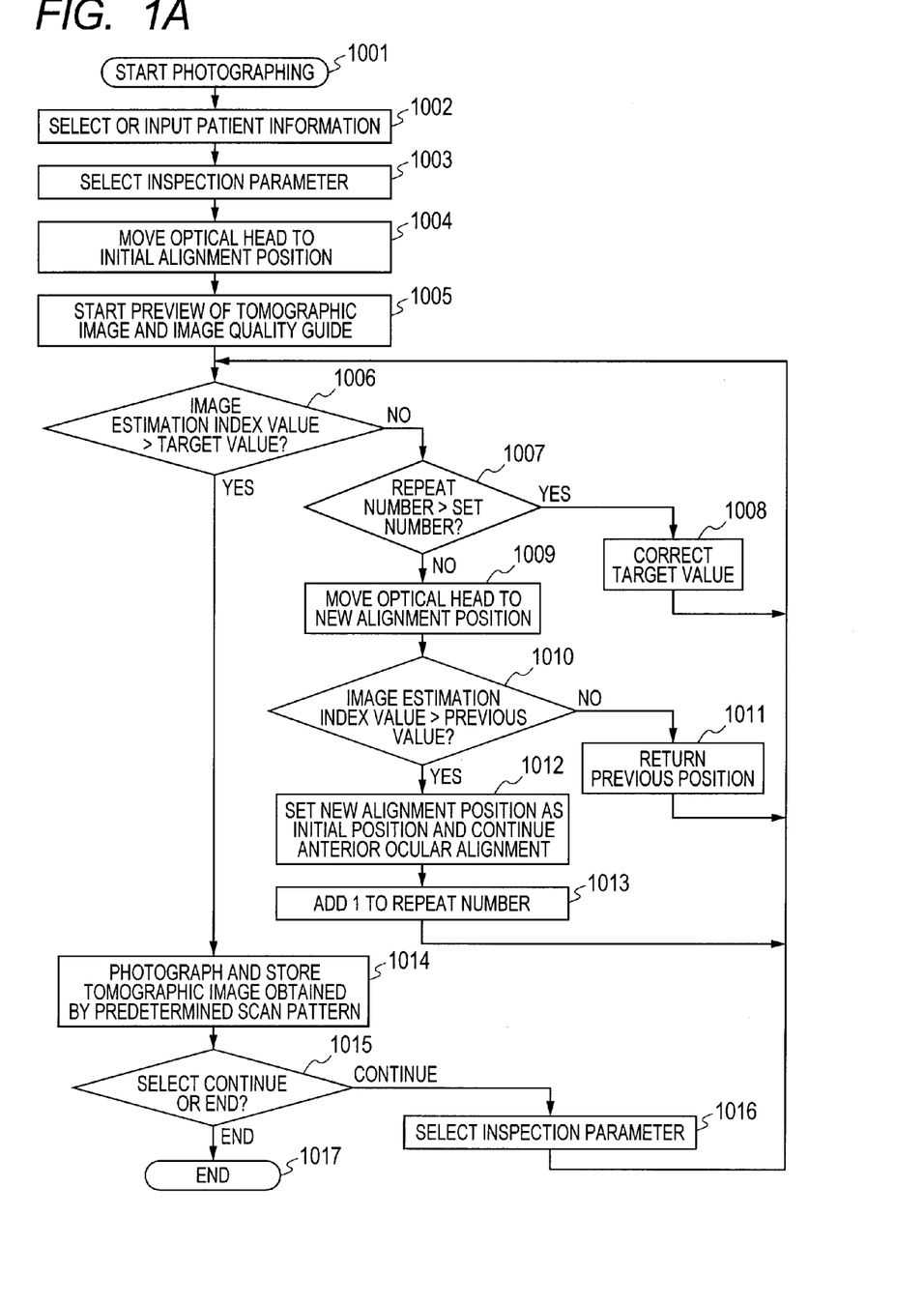
FIG. 1A is a flow diagram for explaining image photographing in examples 1 and 2.

A flow chart of photographing shown in FIG. 1A will be described in order of steps.

Photographing is started in step 1001. A program for photographing is executed by the personal computer 925 to start a screen for photographing on the monitor 928. At the same time, the XY scanner 134 is operated. The flow is automatically transferred to step 1002.

In step 1002, a patient information input screen is displayed on the monitor 928, and the operator selects a patient or inputs patient information if it is a first visit. The flow is transferred to step 1003 by operator's operation (for example, an OK button displayed on the patient information input screen is clicked by a mouse).

In step 1003, an examination parameter select screen is displayed on the monitor. The operator sets a selection of left or right of the eye to be inspected as an examination parameter, a range in which tomographic photographing is performed, the number of times of photographing the tomographic image, the number of the A-scan images included in the B-scan image, and so on. The setting associated with tomographic image photographing is referred to as a scan pattern. The flow is transferred to step 1004 by operator's operation (for example, an OK button displayed on the inspection parameter select screen is clicked by the mouse).

In step 1004, the optical head 900 is moved to the initial alignment position.

Figure 6A:
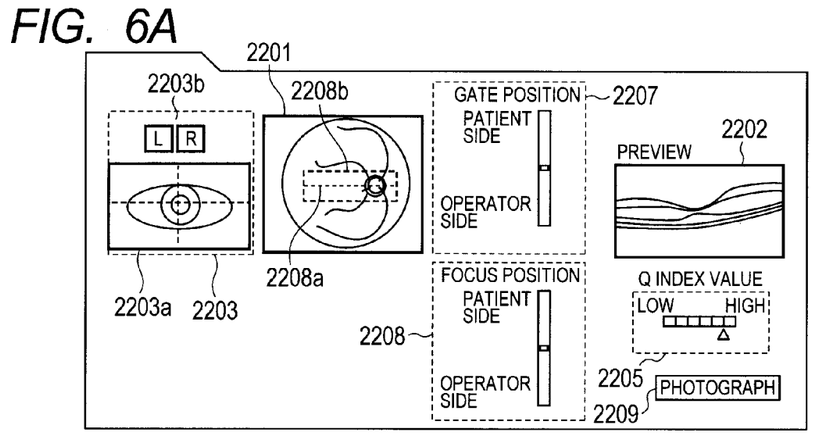
FIGS. 6A, 6B and 6C are views for explaining a screen for alignment in the examples 1 and 2.

A screen for tomographic image photographing exemplified in FIG. 6A is displayed on the monitor 928. In this step, an anterior ocular segment image and a fundus image are displayed. The screen includes an anterior ocular segment image monitor 2203, and an anterior eye image 2203a is displayed on the anterior ocular segment image monitor 2203. A left and right select button 2203b is operated for selecting left or right eye to be inspected and serves as a function of displaying the selected eye with level of brightness. A fundus image 2201 is displayed on the anterior ocular segment image monitor 2203 and includes a position 2208a of the B-scan image of a tomographic image preview to be described later and a tomographic photographing range 2208b selected in step 1003.

Figure 3A:
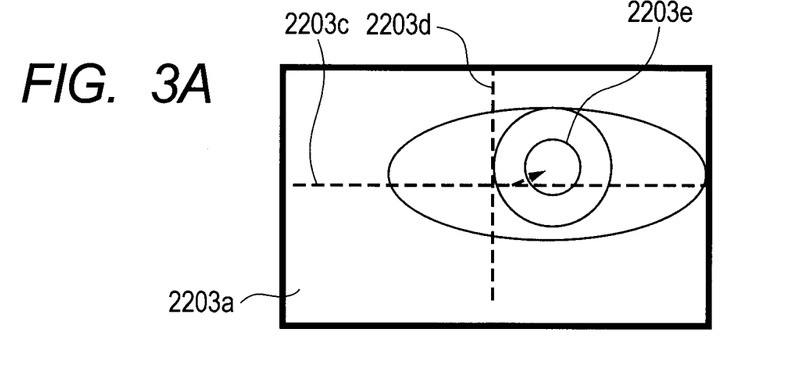
FIGS. 3A, 3B and 3C are views for explaining an anterior ocular segment image during alignment in the examples 1 and 2.
Figure 3B:
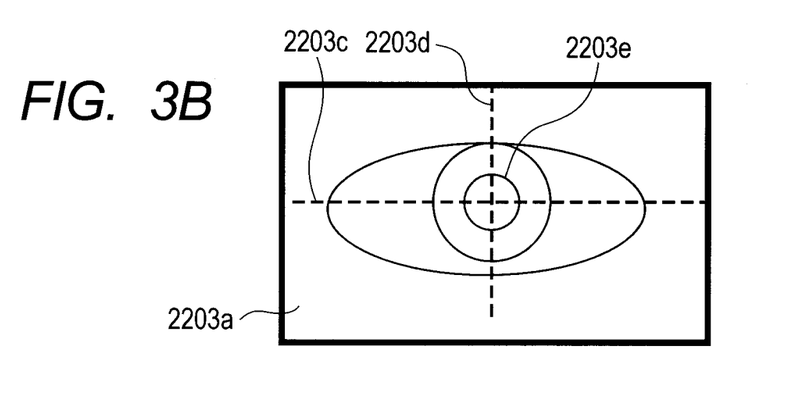

In this step, the optical head 900 is moved to a measurement start position according to the left or right of the eye to be inspected, and an image of an anterior eye portion of the eye to be inspected 107 is photographed by the CCD 171 for anterior eye observation. FIG. 3A shows an example of the image, and the center of the image (displayed at a point at the intersection of an index 2203c with an index 2203d) coincides with the optical axis of the measurement optical system of the optical head 900. The control portion moves the optical head 900 so that the center of a pupil 2203e as an initial adjustment target position coincides with an image center position in the XY directions. The positional alignment between the optical head 900 and the center of the anterior ocular segment image may be relatively performed. Accordingly, the optical head 900 functions as a relative position changing unit which changes the relative position between them and may be moved on the anterior eye side. An example of the anterior ocular segment image after movement of the optical head 900 is shown in FIG. 3B, and the center of the pupil 2203e coincides with the image center. The Z direction is adjusted by moving the optical head 900 based on the size of a bright spot (not shown) on an image projected on the anterior ocular segment. The Z direction is adjusted so that the size of the bright spot is minimum.

The position after alignment of the head portion 200 in this step is the initial alignment position. The center of the pupil 2203e is extracted by image processing. Although FIG. 3B shows a case where the center of the anterior ocular segment image and the optical axis of the optical head 900 coincide with each other, the present invention is not limited to this case, and for example as long as the relative positional deviation is within a previously determined first predetermined range, the subsequent operation may be performed.

Thereafter, the flow is automatically transferred to step 1005.

In step 1005, a preview of the tomographic image and a guide of image quality are displayed on the monitor 928. Namely, after positional adjustment to the initial adjustment target position, an image estimation index of the tomographic image is visualized and displayed on the monitor 928. The personal computer 925 constitutes the tomographic image at the position 2208a based on a signal from the line sensor 182 and displays the tomographic image in a tomographic photographing preview image 2202 of FIG. 6A. An indicator 2205 displays a Q index value as the guide of the image quality of the displayed tomographic photographing preview image 2202. As the indicator 2205 moves rightward, the Q index value of an image becomes higher, and the level of an image quality is visually shown. The Q index is one of OCT image estimation indexes and shows the rate of effective pixels for diagnosis in a histogram of an image. A program calculating the Q index and comparing the calculated Q index with a target value or a value at another alignment position is an image comparing unit in this example. The program is integrated with the program for photographing described above and executed by the personal computer 925 as the device control portion.

Figure 4A:
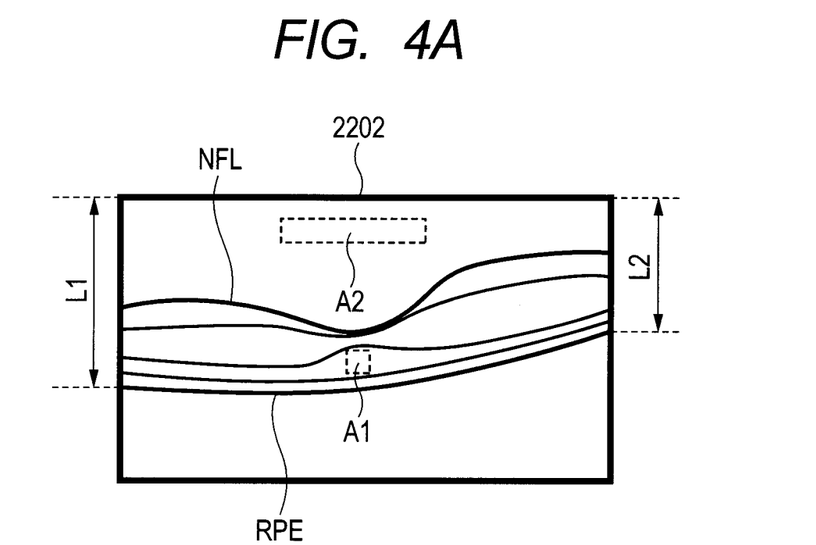
FIGS. 4A and 4B are views for explaining a preview image of a tomographic image during alignment in the examples 1 and 2.

The method of calculating the Q index is described in the following document: British Journal of Ophthalmology 2006, Vol. 90: pp. 186-190, "A new quality assessment parameter for optical coherence tomography." Although the Q index value is used as the guide of the image quality, the following image estimation indexes are considered to be used: (1) SNR, which is an index which has conventionally been used and shows a ratio between a maxim brightness value of an image and a brightness value of a background noise; and (2) local image contrast, which is a contrast which is calculated from an average brightness value of a local region in a retina and an average brightness value of background. The example of the local image contrast will be described with reference to FIG. 4A. FIG. 4A shows the tomographic photographing preview image 2202. A region A1 is a portion of ONL (external granular layer) which is relatively dark in a retinal layer. A region A2 is a portion of a background portion. The contrast is calculated from the average brightness value of the two regions.

The local contrast is not limited to ONL and background. The local contrast may be contrast between an interlayer or a layer required for diagnosis and background and may be set to be allowed to be selected by the operator.

The local image contrast calculation requires segmentation for identifying ONL and so on and confirming a region.

In this step, adjustment of the optical path length of a reference optical path according to the movement of the mirror 132-4, focusing of a fundus image with the use of the lens 135-3, and focusing a tomographic image with the use of the lens 135-5 are performed. Although they are automatically adjusted, a gate position adjustment slider 2207 and a focus position adjustment slider 2208 are provided in the screen as shown in FIG. 6A, and the operator can perform fine adjustment after automatic adjustment.

Then, the flow is automatically transferred to step 1006.

In step 1006, it is determined whether the Q index value that is the image estimation index value is greater than a previously determined target value. When it is determined that the image estimation index value is greater than the target value, that is, when the image is determined to be a good image, the flow proceeds to step 1014. When the image estimation index value is not greater than the target value, that is, when the image is determined to be not good, the flow proceeds to step 1007.

The operation of obtaining the image estimation index value from the tomographic image exemplified above is executed by a module area in the personal computer 925 as the device control part functioning as the image estimation unit.

In step 1007, it is determined whether the number of repeating the alignment fine adjustment routine in steps 1006 to 1012 is larger than a set value. When the repeat count is larger than the set value, the flow is transferred to step 1008. In step 1008 the target value of the image estimation index is corrected downward, and the flow is returned to step 1006. This is because the value may not reach a high image estimation index value in any position according to the eye to be inspected, and in such a case, an automatic alignment motion is converged. When the repeat count is not more than the set value, the flow proceeds to step 1009.

In step 1009, the personal computer 925 outputs a movement instruction for moving the optical head 900 to the stage portion 950 and moves the optical head 900 to a new alignment position according to the moving amount instructed in the movement instruction step. Namely, when it is determined that positional deviation between the center position of the anterior ocular segment image and the optical axis of the optical head 900 is within a first predetermined range, a position to become the center of the anterior ocular segment image in the actual measurement is designated as the new alignment position which is a predetermined position, and the optical head 900 is relatively moved. In the operation, a specified region in the personal computer 925 functions as a designating unit of the present invention. The automatic alignment function for the anterior eye is temporarily stopped before the optical head 900 is moved.

A method of obtaining the new alignment position will be described. For example, in some case, a tomographic image is inclined on a screen. This case will be described exemplifying a case of photographing a yellow spot neighborhood portion with reference to FIGS. 5A to 5C.

Figure 4B:
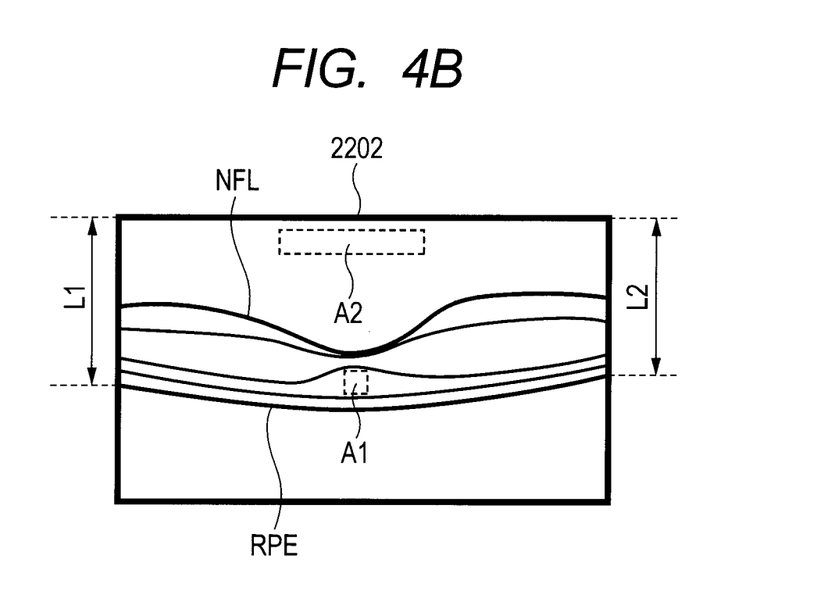
Figure 5A:
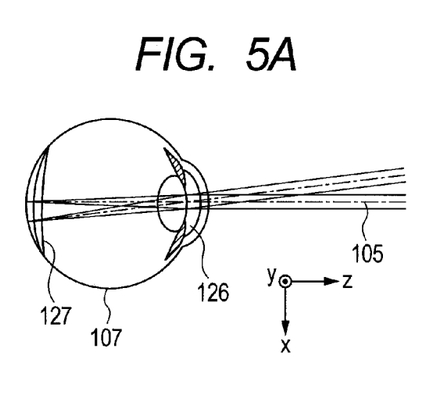
FIGS. 5A, 5B, 5C, 5D and 5E are views for explaining an eye to be inspected and light beams for observation in the examples 1 and 2.
Figure 5B:
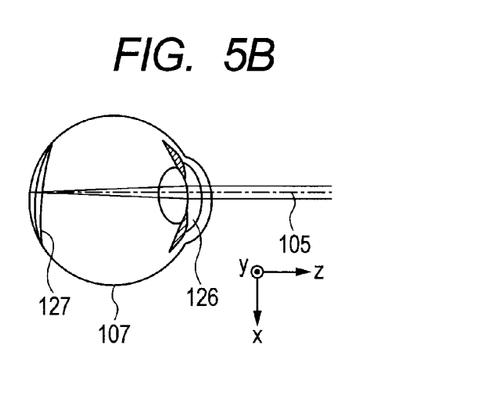

In FIG. 5A, if the visual axis of the eye to be inspected 107 is not inclined with respect to the measurement light 105, when the center of the yellow spot is photographed by fixation, incident light and the yellow spot neighborhood portion of a retina 127 are substantially perpendicular, and therefore, the intensity of return light is large, and a high signal intensity is obtained. Meanwhile, in the eye to be inspected 107 with the inclined visual axis, as shown in FIG. 5B, when the measuring or incident light 105 reaches the retina 127, the yellow spot neighborhood portion is inclined with respect to the optical axis of the incident light, whereby the signal intensity is lowered, and at the same time, the tomographic image is often inclined as shown in FIG. 4A. In this case, the Q index as the image estimation index is low. The distance of an image end portion of a RPE (retinal pigment epithelia) layer in which the brightness on the tomographic image is the highest according to the segmentation is compared to move the optical head 900. In this case, the optical head 900 functions as the inclination changing unit in the present invention. When the optical head 900 changes the inclination, a predetermined position is designated by the designating unit according to the change. The optical head 900 is moved so that a distance L1 at the left end from a leftmost upper portion (gate position) of the image in FIG. 4A to the RPE layer and a distance L2 of a right end portion are substantially equal to each other. FIG. 4B shows an example after the movement of the optical head 900 and a case where the optical head 900 is moved by a distance d in the X direction from the initial alignment position. The incident light 105 substantially perpendicularly enters the yellow spot neighborhood portion, and as shown in FIG. 4B, the distances L1 and L2 at the both ends are substantially equal to each other. The Q index value often becomes high under the condition.

Although the example in which automatic inclination correction is performed based on the distance from the upper portion of the image to the RPE layer is shown, when paying attention to NFL (nerve fiber layer) such as glaucoma testing, the automatic inclination correction may be performed based on the distance from the upper portion of the image to the NFL.

In the drawings, although only the case associated with the X direction is explained, the inclination correction may be performed in the X direction or the Y direction or both the X and Y directions. In order to confirm the movement in the Y direction, a preview of a tomographic image which is a cross section in the Y direction is required to be photographed.

In this state, the flow is automatically transferred to step 1010.

In step 1010, the image estimation index value is compared with a value before movement (previous value) in step 1009. When the image estimation index value is smaller than a previous value, the flow is transferred to step 1011. When the image estimation index value is larger than the previous value, the flow is transferred to step 1012.

In step 1011, the optical head 900 is moved to a previous position. At this time, in order to prevent the moving amount from being the same as the present moving amount, change may be performed so that a correction amount to be calculated is multiplied by a coefficient giving weight. For example, a value obtained by multiplying the correction amount, calculated from inclination, by a coefficient of 0.5 may be used as an actual moving amount. Since the image estimation index may be lowered by factors other than the inclination, the next setting may be performed so that the optical head 900 is moved by a fixed step amount.

In step 1012, when described using the above example, the anterior eye automatic alignment at a position separated by the distance d from the center of the pupil, that is, the new alignment position, is started, and the anterior eye automatic alignment is continuously photographed.

Namely, the alignment position is transferred to a new adjustment target position set by the movement of the optical head 900, and the automatic alignment as positional adjustment is executed based on this.

According to the above constitution, even in the tomographic photographing requiring a relatively long photographing time, photographing can be performed while maintaining a good state of the resulting image. The distance d from the center of the pupil showing the new alignment position is temporarily stored.

Figure 3C:
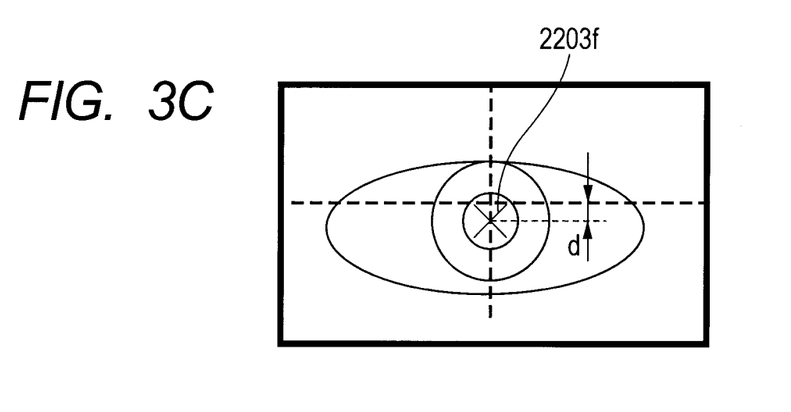

FIG. 3C shows an anterior eye image 2203a at that time. A mark 2203f showing the new alignment position is displayed at a position separated by the distance d from the center of the pupil 2203e, whereby the continuation of the alignment at a new position is clearly demonstrated to the operator. Namely, the anterior eye image is displayed on the monitor 928, and the adjustment target position is displayed on the anterior ocular segment image. In the present invention, in the movement of the optical head 900 as the relative position changing unit to the new alignment position specified as the adjustment target position or a predetermined position, the alignment operation is performed so that a deviation amount between the predetermined position and the optical axis of the optical head 900 falls within a designated second predetermined range. The predetermined position previously corresponds to the position designated as a predetermined position in the anterior ocular segment image. The second predetermined range may coincide with the first predetermined range. Alternatively, the second predetermined range is set again or previously designated, whereby it may be a range different from the first predetermined range. Those operations are executed by the region functioning as the control unit in the personal computer 925. Thereafter, the flow is automatically transferred to step 1013.

One is added to the repeat count in step 1013, and the flow is returned to step 1006.

Then, steps 1006 to 1013 are repeated, and the flow is finally transferred to step 1014.

In step 1014, a tomographic image is photographed by a scan pattern set in step 1003, and, at the same time, the tomographic image is stored in a storage device in the personal computer 925. The storing operation may be performed automatically or by clicking a photographing button 2209 with a mouse. The flow is automatically transferred to step 1015.

In step 1015, a screen on which continuation of the inspection or termination of the inspection is selected is displayed, and the operator selects either one of them. The photographed tomographic image may be displayed at this stage. When the inspection is continued, the flow is transferred to step 1016. In step 1016, an inspection parameter for the next photographing is set, and the flow is returned to step 1006. When the inspection is to be ended, the flow is transferred to step 1017, and the inspection is ended.

The above flow is a flow of photographing in the fundus inspection apparatus in this example.

The new alignment position stored for each update is stored as the adjustment target position for each subject and patient information in a hard disk 926 in the personal computer 925. Consequently, when the same eye is inspected, the automatic alignment is started using the new alignment position as the initial adjustment target position in the reexamination, so that the automatic alignment can be started from such a state that the Q index value is high. For example, in FIG. 5A, since the automatic alignment can be started not from the center of the pupil but the position distance d away from the center of the pupil, the inspection time is shortened, whereby the burden of a subject can be reduced.

Although the Q index value is improved by automatically correcting the inclination, the automatic alignment in another point of view is considered in order to increase the Q index value. For example, there is automatic alignment for avoiding partial opacification of crystalline lens due to cataract.

This will be described using FIGS. 5D and 5E. Partial opacification 110 is shown in FIGS. 5D and 5E. FIG. 5D shows a state that the positional adjustment of the eye to be inspected 107 and the optical head 900 is performed in step 1004. FIG. 5D shows a case in which the partial opacification 110 due to cataract exists particularly at an optical path central portion, and the light beams 105 of the measurement light for tomographic photographing are scattered, and most of the light beams do not reach the fundus 127. Accordingly, at the same time when a tomographic photographing preview image is much darkened, the Q index value is lowered. In this case, the new alignment position in step 1007 is a position where the optical head is moved by a previously determined step amount from the actual position. For example, when the distance is d, the optical head 900 is moved by approximately 0.5 mm in the X or Y direction. The movement is repeated, whereby the optical head position can lead the measuring light 105 for tomographic image photographing to the fundus so that the optical head can avoid the opacification 110 (FIG. 5E). Accordingly, the tomographic photographing can be performed at the position where the Q index value is high. The automatic alignment can continuously be performed at the position where the opacification is avoided, and therefore, even in the tomographic photographing requiring a relatively long photographing time, photographing can be performed while a good state of an image to be obtained is maintained. Since the automatic adjustment for detecting the position where the opacification is avoided basically takes a longer time than the inclination correction in which a movement distance can be estimated, the continuation of the automatic alignment is more effective in time reduction than the inclination correction.

As descried above, a good tomographic layer can automatically be photographed, and the automatic alignment for obtaining the good tomographic image can continuously be performed.

From the standpoint of an operator, the operator can easily use the fundus inspection apparatus, and the examination time is shortened to reduce the burden of a subject.

Namely, the position where a good tomographic image can be photographed can automatically be detected, whereby an operator can perform operation more easily.

Further, an operator can finely adjust the alignment position, and a position where a good tomographic image can be photographed can be detected more directly.

Furthermore, the image estimation index of a tomographic image is visualized and displayed, whereby an operator can easily judge whether the tomographic image is good.

The adjustment target position is displayed along with the anterior ocular segment image, whereby an operator can easily confirm whether the alignment function effectively acts.

When a tomographic image is stored, the adjustment target position is stored for each operator. When the subject information is called up in the reexamination, the adjustment target position is called up at the same time and used as the initial adjustment target position in the reexamination, whereby the alignment time in the reexamination is shortened to reduce the burden of the subject.

Example 2

The fundus inspection apparatus in this example is different from the example 1 in the flow of the tomographic image photographing. Specifically, an operator determines the good alignment position from the initial alignment position. The descriptions other than those of the flow and the photographing operation screen view are common to those of the example 1. Since the other device configuration is similar to the example 1, the description is omitted.

(Flow of Photographing Tomographic Image)

Figure 1B:
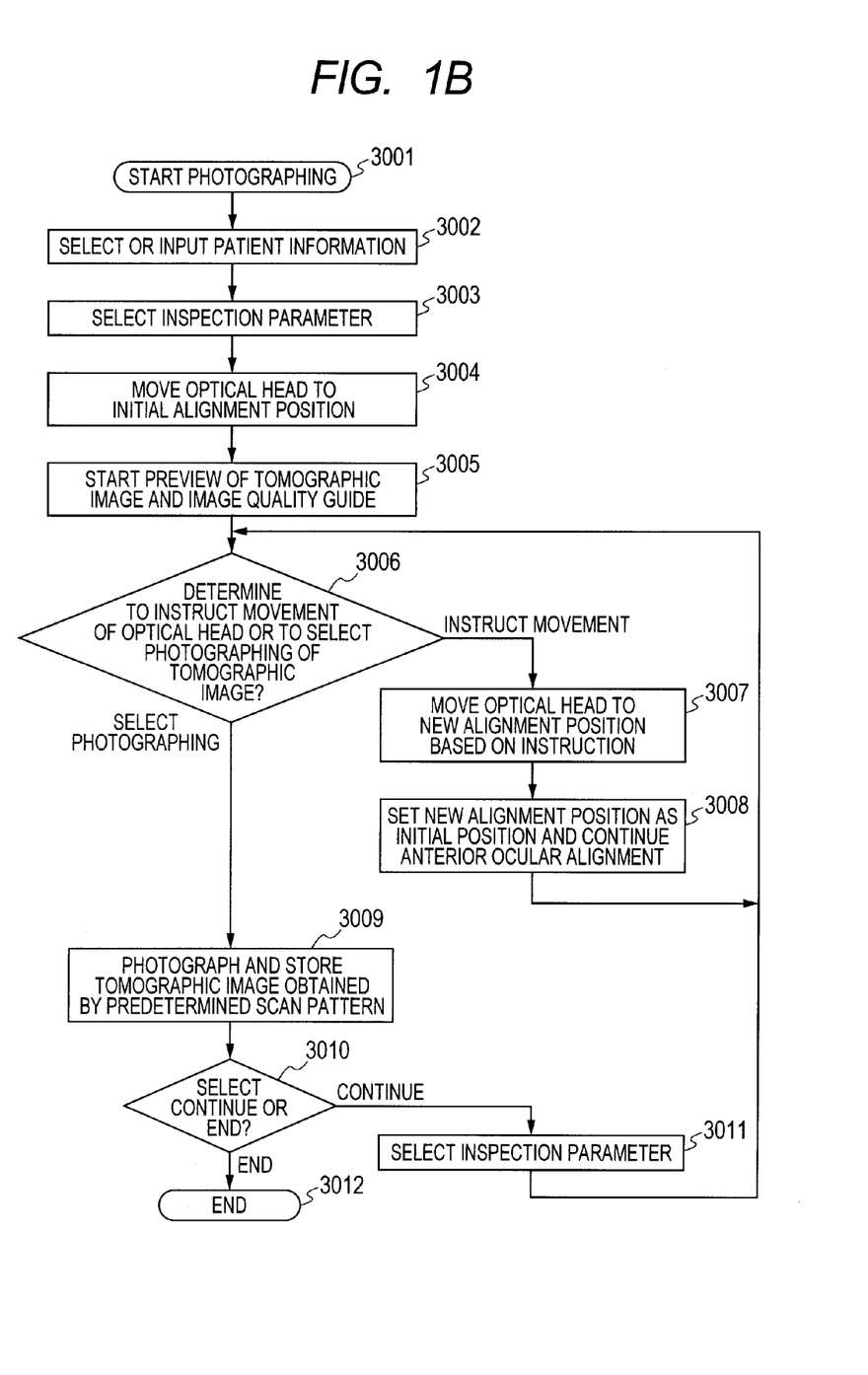
FIG. 1B is a flow diagram for explaining image photographing in the examples 1 and 2.

A flow chart of photographing shown in FIG. 1B will be described in order of steps.

Figure 6B:
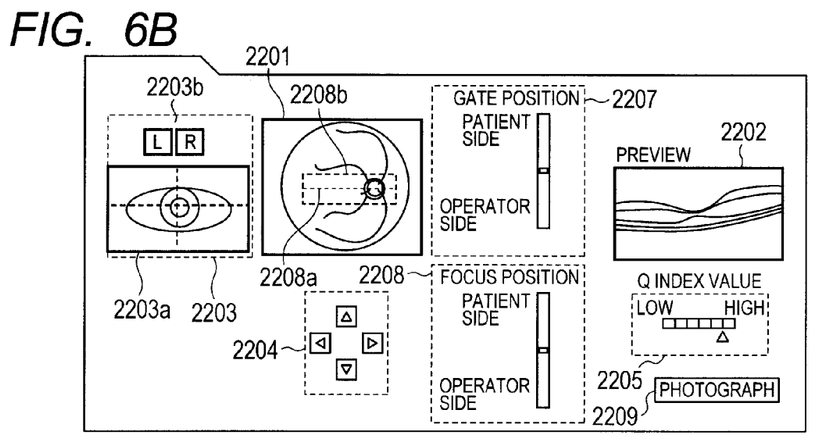

FIG. 6B shows an operation screen for tomographic photographing in this example. This example is different from the example 1 in that there is an optical head movement button 2204 for operating the movement of an optical head 900 by an operator.

Since steps 3001 to 3005 are similar to steps 1001 to 1005 in the example 1, the description is omitted.

In step 3006, the operator refers to a preview 2002 of a tomographic image in FIG. 6B and a display of a Q index value indicator 2205 and thereby determines either photographing of a tomographic image or movement and adjustment of the optical head 900 from the initial alignment state so that the image quality is further improved. When the tomographic image is photographed, a photographing button 2209 is clicked by a mouse, so that the flow is transferred to steps 3009 and 3010. Meanwhile, when the operation is not performed, in the movement and adjustment of the optical head 900 from the initial alignment state, the operator provides an instruction for moving the position of the optical head 900. Specifically, the optical head movement buttons 2204 are operated. For example, in the state of FIG. 4A, a leftward movement button of the optical head movement buttons 2204 is clicked by the mouse, or the clicking is continued. In such case, the flow is automatically transferred to step 3007.

Figure 5C:
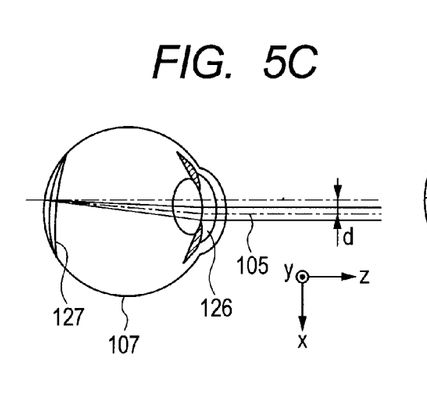
Figure 5D:
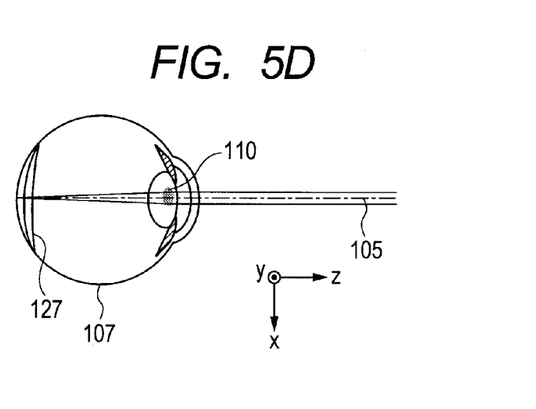
Figure 5E:
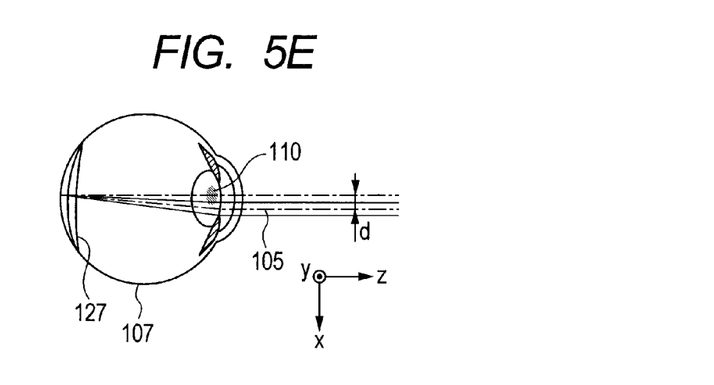

In step 3007, an optical head 900 is moved in the positive direction of an X axis shown in FIG. 5C corresponding to operator's operation, whereby the inclination of the tomographic image is corrected to the state of FIG. 4B. In this case, the Q index value is increased, and this is reflected in the indicator 2205. The flow is automatically transferred to step 3008. Meanwhile, the alignment operation according to the anterior eye is temporarily stopped before the movement of the optical head 900.

In step 3008, when the operator performs operation, the distance d from an initial alignment position is stored as a new alignment position at every operator's operation. The anterior eye alignment is started again while keeping the position and continued. Then the flow is returned to step 3006.

Steps 3006 to 3008 are repeated, and once the tomographic image becomes good, the operator clicks the photographing button 2209 with the mouse. The device photographs a tomographic image according to a set scan pattern and stores the photographed tomographic image in a personal computer 925. Then, the flow is automatically transferred to step 3010.

Steps 3010, 3011, and 3012 are similar to the steps in the example 1 and correspond to steps 1015, 1016, and 1017, respectively. Accordingly, the description is omitted.

The above flow is the photographing flow of the present example.

As in the example 1, when the tomographic image is stored, the new alignment position stored for each update is stored in a storage device 926 in the personal computer 925 along with the patient information. According to this constitution, when the same eye is inspected, an operator can perform fine adjustment from the state that the image quality of the new alignment position, that is, the tomographic image, is relatively high, whereby the inspection time at revisit can be reduced.

As described above, even when an operator finely adjusts the alignment position of the optical head 900 with respect to the eye to be inspected in order to obtain a good tomographic image, the good automatic alignment with respect to the eye to be inspected can be achieved.

Further, as in the example 1, from the standpoint of an operator, the operator can easily use the fundus inspection apparatus, and from the standpoint of a subject, the inspection time is shortened to reduce the burden of the subject.

Another example of the operation in steps 3006 and 3007 will be described.

Figure 6C:
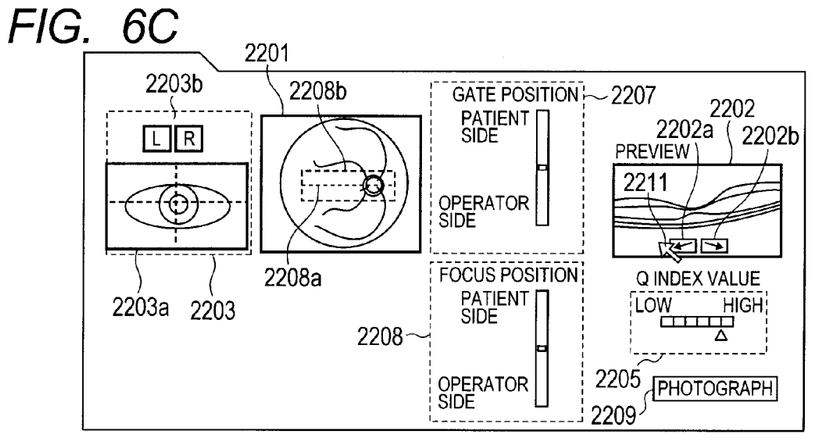

With regard to the inclination of the tomographic image, the optical head movement button 2204 is not operated, but the constitution shown in FIG. 6C may be provided so that the operation can be understood more intuitively. FIG. 6C shows a movable mouse cursor 2211, which designates a designating portion on a screen by operator's operation with a mouse, and inclination adjustment buttons 2202a and 2202b. The mouse cursor 2211 is located near the inclination adjustment buttons 2202a and 2202b, whereby a first tomographic image 2002 is displayed. For example, since the right end side of the tomographic image 2002 rises, the inclination adjustment button 2202b is clicked, or the clicking is continued. The optical head 900 is moved based on the instruction to lower the right end of the tomographic image. By virtue of the adjustment, the tomographic image can be adjusted to one that is considered to be good by an operator. After completion of the inclination adjustment operation, when the mouse cursor 2211 is separated from the vicinity of the inclination adjustment buttons 2202a and 2202b, the information of the tomographic image can be displayed on the entire screen in such a state that the inclination adjustment buttons 2202a and 2202b are not displayed.

Other Example

The present invention is also realized by executing the following processing. Namely, in the processing, a software (program) realizing the functions of the above embodiments is supplied to a system or an apparatus through a network or various storage media, and a computer (or CPU, MPU, or the like) of the system or the apparatus reads out programs and executes the programs.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-077097, filed Mar. 31, 2011, which is hereby incorporated by reference herein in its entirety.

What is claimed is:

1. An ophthalmologic apparatus comprising:
a tomographic image acquisition unit configured to obtain a tomographic image of a fundus of an eye to be inspected based on combined light obtained by combining (a) return light from the eye to be inspected irradiated with measuring light and (b) reference light corresponding to the measuring light;
a position alignment unit configured to execute a first alignment between a first position on a pupil of the eye to be inspected and the tomographic image acquisition unit, in an XY plane orthogonal to a depth direction of the fundus of the eye to be inspected;
a display control unit configured to cause a display unit to display, at the same time, (a) the tomographic image and (b) a graphical user interface used for receiving an instruction to change an inclination of the tomographic image displayed on the display unit, wherein the graphical user interface comprises two indicators designating different directions from each other, and the directions designated by the indicators are directions in which incline of the tomographic image is displayed on the display unit; and
a control unit configured to cause the position alignment unit to change a positional relation between the tomographic image acquisition unit and the pupil of the eye to be inspected in the XY plane so as to execute a second alignment between a second position on the pupil of the eye to be inspected and the tomographic image acquisition unit, based on the instruction received by the graphical user interface, the second position being different from the first position in the XY plane,
wherein, by changing the positional relation from a state after the first alignment to a state after the second alignment, a position on the pupil in the XY plane where the measuring light is incident is changed from the first position to the second position, an incident angle to the fundus of the measuring light is changed, and a position on the fundus where the measuring light is incident is not changed,
wherein the inclination of the tomographic image displayed on the display unit is changed by changing the positional relation from the state after the first alignment to the state after the second alignment, and wherein, after changing the positional relation from the state after the first alignment to the state after the second alignment, the position alignment unit automatically continues to execute the second alignment between the second position on the pupil of the eye to be inspected and the tomographic image acquisition unit.

2. An ophthalmologic apparatus according to claim 1, wherein the first position corresponds to a center position of the pupil of an anterior ocular segment of the eye to be inspected.

3. An ophthalmologic apparatus according to claim 1, wherein the graphical user interface receives the instruction through a mouse, and
wherein the change of the inclination of the tomographic image displayed on the display unit is instructed by clicking one of the indicators on the graphical user interface through the mouse.

4. An ophthalmologic apparatus according to claim 3, wherein the display control unit causes the display unit to display (a) the graphical user interface on the tomographic image and (b) a mouse cursor of the mouse, and
wherein the display control unit causes the graphical user interface to disappear based on a position of the mouse cursor.

5. An ophthalmologic apparatus according to claim 1, wherein the display control unit causes the display unit to display an index representing a quality of the tomographic image displayed on the display unit.

6. An ophthalmologic apparatus according to claim 5, wherein the display control unit causes the display unit to display, with the tomographic image, the index representing the quality of the tomographic image.

7. An ophthalmologic apparatus according to claim 1, wherein the position alignment unit executes the first alignment and the second alignment by moving the tomographic image acquisition unit.

8. An ophthalmological apparatus according to claim 1, wherein each of the two indicators comprises a graphical user interface button.

9. An ophthalmological apparatus according to claim 1, wherein each of the two indicators comprises a graphical user interface button which is clickable by a user using a mouse cursor.

10. A control method for controlling an ophthalmologic apparatus, the control method comprising the steps of:
obtaining, by a tomographic image acquisition unit, a tomographic image of a fundus of an eye to be inspected based on combined light obtained by combining (a) return light from the eye to be inspected irradiated with measuring light and (b) reference light corresponding to the measuring light;
executing, by a position alignment unit, a first alignment between a first position on a pupil of the eye to be inspected and the tomographic image acquisition unit, in an XY plane orthogonal to a depth direction of the fundus of the eye to be inspected;
controlling a display unit to display, at the same time, (a) the tomographic image and (b) a graphical user interface used for receiving an instruction to change an inclination of the tomographic image displayed on the display unit, wherein the graphical user interface comprises two indicators designating different directions from each other, and the directions designated by the indicators are directions in which incline of the tomographic image is displayed on the display unit; and causing the position alignment unit to change a positional relation between the tomographic image acquisition unit and the pupil of the eye to be inspected in the XY plane so as to execute a second alignment between a second position on the pupil of the eye to be inspected and the tomographic image acquisition unit, based on the instruction received by the graphical user interface, the second position being different from the first position in the XY plane, wherein, by changing the positional relation from a state after the first alignment to a state after the second alignment, a position on the pupil in the XY plane where the measuring light is incident is changed from the first position to the second position, an incident angle to the fundus of the measuring light is changed, and a position on the fundus where the measuring light is incident is not changed, wherein the inclination of the tomographic image displayed on the display unit is changed by changing the positional relation from the state after the first alignment to the state after the second alignment, and wherein, after changing the positional relation from the state after the first alignment to the state after the second alignment, the position alignment unit automatically continues to execute the second alignment between the second position on the pupil of the eye to be inspected and the tomographic image acquisition unit.

11. A non-transitory tangible medium having recorded thereon a program for causing a computer to perform steps of the control method according to claim 10.

* * * * *